United States Patent [19]

Roling

[11] Patent Number: 4,912,247

[45] Date of Patent: Mar. 27, 1990

[54] ENHANCEMENT OF AROMATIC AMINE INHIBITION OF ACRYLATE MONOMER POLYMERIZATION BY ADDITION OF MANNICH PRODUCTS

[75] Inventor: Paul V. Roling, Spring, Tex.

[73] Assignee: Betz Laboratories, Ltd., Trevose, Pa.

[21] Appl. No.: 299,484

[22] Filed: Jan. 19, 1989

[51] Int. Cl.[4] ................... C07C 121/32; C07C 67/62; C09K 15/22

[52] U.S. Cl. ............................ 558/306; 252/182.28; 252/182.29; 252/403; 560/4; 560/205

[58] Field of Search ................. 560/4, 205; 558/306; 252/182.28, 182.29, 403

[56] References Cited

U.S. PATENT DOCUMENTS

| | | | |
|---|---|---|---|
| 3,674,651 | 4/1972 | Otsuki et al. | 203/8 |
| 3,855,281 | 12/1974 | Sullivan et al. | |
| 3,876,686 | 4/1975 | Sato | 560/4 |
| 3,959,358 | 5/1976 | Jursich | 560/4 |
| 4,016,198 | 4/1977 | Wilder | 560/4 |
| 4,051,067 | 9/1977 | Wilder | 252/401 |
| 4,267,365 | 5/1981 | Findeisen | 560/205 |
| 4,310,676 | 1/1982 | Schropp | 560/4 |
| 4,789,695 | 12/1988 | Farrer et al. | 523/336 |

*Primary Examiner*—Werren B. Lone
*Assistant Examiner*—Vera C. Clarke
*Attorney, Agent, or Firm*—Alexander D. Ricci; Gregory M. Hill

[57] ABSTRACT

A composition and method of use for inhibiting the polymerization of acrylate esters during elevated temperature processing and during storage and handling thereafter.

It comprises the combination of a Mannich reaction product, which is prepared from a substituted phenol, an aldehyde and ethylenediamine, and either phenylenediamine or derivatives thereof and/or phenothiazine or derivatives thereof.

36 Claims, No Drawings

ENHANCEMENT OF AROMATIC AMINE INHIBITION OF ACRYLATE MONOMER POLYMERIZATION BY ADDITION OF MANNICH PRODUCTS

FIELD OF THE INVENTION

The present invention relates to a composition and method of inhibiting polymerization of acrylate monomers.

It is well known in the art that acrylate monomers, particularly acrylate esters, readily polymerize and that the rate of polymerization increases with increasing temperature. Common industrial methods for producing the acrylate esters typically include purification processing such as distillation to remove impurities. However, purification operations carried out at elevated temperatures result in an increased rate of undesirable polymerization. The polymerization of acrylate esters is undesirable because it causes fouling of the processing equipment and it renders the compounds unfit for use without further treatment.

PRIOR ART

Known polymerization inhibitors for acrylate esters include phenylenediamines, phenothiazine, methylene blue, hydroquinone, the methyl ether of hydroquinone (MEHQ), benzoquinone, and alkylamines.

Phenylenediamines alone or with oxygen are known in the art as polymerization inhibitors in acrylate systems. Otsuki et al in U.S. Pat. No. 3,674,651 disclose a process for inhibiting the polymerization of acrylic acid using a combination of N,N'-diphenyl-p-phenylenediamine or its derivatives and an oxygen-containing gas, or mixtures of N,N'-diphenyl-p-phenylenediamine or its derivatives with benzoquinone and/or hydroquinone monomethyl ether (MEHQ) and an oxygen-containing gas.

Sullivan et al in U.S. Pat. No. 3,855,281 disclose the use of various phenylenediamines as polymerization inhibitors of unsaturated carboxylic acid esters.

Of primary interest are U.S. Pat. Nos. 4,016,198 and 4,051,067 (both to Wilder) which disclose the use of a combination of a polyalkyleneamine and an arylenediamine for stabilization of unsaturated carboxylic esters. The polyalkyleneamine contributed little inhibition activity on its own but the combination of the polyalkyleneamine and the arylenediamine was about twice as effective in most cases as the arylenediamine alone. The polyalkyleneamines claimed were diethylenetriamine and other amines with three or more nitrogens.

In U.S. Pat. No. 3,959,358, acrylate esters were stabilized by combinations of phenothiazine or phenylenediamines with phenols such as p-methoxyphenol. Phenothiazine was used as a stabilizer of oligomeric acrylic acids in U.S. Pat. No. 4,267,365.

Hexamethylenetetramine was used to inhibit polymerization of acrylate esters in U.S. Pat. No. 3,876,686.

SUMMARY OF THE INVENTION

This invention relates to a composition and method of use for inhibiting acrylate ester polymerization comprising adding an effective amount for the purpose of (a) a Mannich product prepared from a substituted phenol having the formula

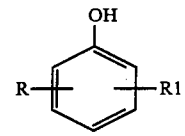

wherein R and R1 are the same or different and are independently selected from hydrogen, hydroxy, alkyl, aryl, alkaryl, aralkyl, or alkoxy groups of from about 1 to 20 carbon atoms and both R and R1 cannot be hydrogen, an aldehyde having the chemical formula

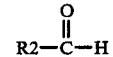

wherein R2 is selected from hydrogen and alkyl groups having from 1 to 6 carbon atoms, and ethylenediamine, and (b) a phenylenediamine or derivatives thereof having the formula

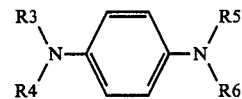

wherein R3, R4, R5, and R6 are the same or different and are hydrogen, alkyl, aryl, alkaryl, aralkyl groups with the proviso that at least one of R3, R4, R5, or R6 is hydrogen, and/or phenothiazine or derivatives thereof having the formula

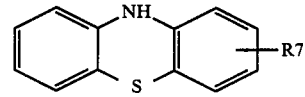

wherein R7 is hydrogen or alkyl.

This mixture provides an unexpectedly higher degree of polymerization inhibition of the acrylate esters than the individual ingredients comprising the mixture. It is therefore possible to produce a more effective acrylate ester polymer inhibiting method than is obtainable by the use of any one ingredient alone. Due to the enhanced polymer inhibiting activity of the mixture, the concentrations of each of the ingredients may be lowered and the total quantity of the polymerization inhibitor required for an effective treatment may be reduced.

Accordingly, it is an object of the present invention to provide methods for inhibiting the polymerization of acrylate esters. Another compound that the invention conceptually should prevent polymerization of is acrylonitrile. The CN group of acrylonitrile functions in much the same way as the -COOR group of the acrylate esters. It is another object of this invention to control fouling of processing equipment due to polymerization. It is a further object of the present invention to provide economically effective polymer inhibiting methods. These and other objects and advantages of the present invention will be apparent to those skilled in the art upon reference to the following detailed description of the invention, which demonstrates the synergism of the compounds comprising the instant invention.

DETAILED DESCRIPTION OF THE INVENTION

The Mannich products of the invention include mixtures of products prepared by a condensation reaction resulting from heating together a phenol, an aldehyde and ethylenediamine.

The substituted phenols used in the preparation of the Mannich products have the chemical formula

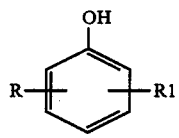

wherein R and R1 are the same or different and are independently selected from hydrogen, hydroxy, alkyl, aryl, alkaryl, aralkyl, or alkoxy groups of from about 1 to 20 carbon atoms and both R and R1 cannot be hydrogen, include p-cresol, m-cresol, o-cresol, p-octylphenol, p-nonylphenol, p-decylphenol, p-dodecylphenol, 2,4-dimethylphenol, 2,4-di-t-butylphenol, 2,4-dinonylphenol, catechol, p-t-butyl-catechol, hydroquinone, p-methoxyphenol, and 2-t-butyl-4-methoxyphenol. The preferred phenol is p-nonylphenol.

The aldehyde component of the Mannich products include formaldehyde, acetaldehyde, propanaldehyde, butylaldehyde, hexaldehyde, heptaldehyde, etc. with the most preferred aldehyde being formaldehyde which may be used in its monomeric form, or, more conveniently in its polymeric form (i.e. paraformaldehyde).

The amine used in preparing the Mannich products is ethylenediamine (EDA).

The molar ratio of substituted phenol: EDA: aldehyde is in the range of 0.5–5: 1: 0.5–5, preferably 1–4:1 :1–4. Optimal results are obtained with a ratio of 2:1:2.

The phenylenediamine component of the inhibitor mixtures of this invention include phenylenediamine and derivatives thereof having at least one N—H group. It is thought that o-phenylenediamine or derivatives thereof having at least one N—H group are suitable in accordance with the instant invention. However, the preferred phenylenediamine is p-phenylenediamine having the formula

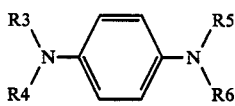

wherein R3, R4, R5, and R6 are the same or different and are hydrogen, alkyl, aryl, alkaryl, aralkyl groups with the proviso that at least one of R3, R4, R5, or R6 is hydrogen, more preferably the alkyl, aryl, alkaryl, and aralkyl groups have one to about twenty carbon atoms. The alkyl, aryl, alkaryl, and aralkyl groups may be straight or branched-chain groups. Exemplary p-phenylenediamines include p-phenylenediamine wherein R1, R2, R3, and R4 are hydrogen; N-phenyl-N'-alkyl-p-phenylenediamines such as,
N-phenyl-N'-methyl-p-phenylenediamine,
N-phenyl-N'-ethyl-p-phenylenediamine,
N-phenyl-N'-propyl-p-phenylenediamine,
N-phenyl-N'-isopropyl-p-phenylenediamine,
N-phenyl-N'-n-butyl-p-phenylenediamine,
N-phenyl-N'-isobutyl-p-phenylenediamine,
N-phenyl-N'-sec-butyl-p-phenylenediamine,
N-phenyl-N'-tert-butyl-p-phenylenediamine,
N-phenyl-N'-n-pentyl-p-phenylenediamine,
N-phenyl-N'-n-hexyl-p-phenylenediamine,
N-phenyl-N'-(1-methylhexyl)-p-phenylenediamine,
N-phenyl-N'-(1,3-dimethylbutyl)-p-phenylenediamine,
N-phenyl-N'-(1,4-dimethylpentyl)-p-phenylenediamine;
N-phenyl-N',N'-dialkyl-p-phenylenediamines, such as
N-phenyl-N',N'-dimethyl-p-phenylenediamine,
N-phenyl-N',N'-diethyl-p-phenylenediamine;
N-phenyl-N',N'-di-n-butyl-p-phenylenediamine,
N-phenyl-N',N'-di-sec-butyl-p-phenylenediamine,
N-phenyl-N'-methyl-N'-ethyl-p-phenylenediamine;
N,N-dialkyl-p-phenylenediamines such as
N,N-dimethyl-p-phenylenediamine and
N,N'-diethyl-p-phenylenediamine;
N,N'-dialkyl-p-phenylenediamines such as
N,N'-di-isopropyl-p-phenylenediamine;
N,N'-diaryl-p-phenylenediamines such as
N,N'-diphenyl-p-phenylenediamine;
N,N,N'-trialkyl-p-phenylenediamines such as
N,N,N'-trimethyl-p-phenylenediamine,
N,N,N'-triethyl-p-phenylenediamine.

Preferably, the p-phenylenediamine is selected from the group consisting of N-phenyl-N'-(1-3-dimethylbutyl)-p-phenylenediamine and N-phenyl-N'-(1,3-dimethylpentyl)-p-phenylenediamine.

Phenothiazine or derivatives thereof have the formula

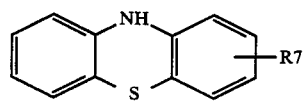

wherein R7 is hydrogen or alkyl. Such phenothiazine compounds can include phenothiazine wherein R7 is hydrogen or 2-methylphenothiazine as exemplary compounds.

The present invention is applicable to readily polymerizable acrylate esters. The term "acrylate ester" as used wherein is intended to include the various esters of acrylic acid and methacrylic acid. Such acrylate esters can include n-alkyl, secondary and branched-chain alkyl esters of acrylic acid and methacrylic acid. Exemplary esters of acrylic acid include methyl acrylate, ethyl acrylate, n-propyl acrylate, iso-propyl acrylate, n-butyl acrylate, iso-butyl acrylate, sec-butyl acrylate, 2-methylbutyl acrylate, 3-methylbutyl acrylate, 2-ethylbutyl acrylate, 1,3-dimethylbutyl acrylate, n-pentyl acrylate, n-hexyl acrylate, n-heptyl acrylate, 1-methylheptyl acrylate, 2-ethylhexyl acrylate, n-octyl acrylate, n-decyl acrylate, n-dodecyl acrylate, n-hexadecyl acrylate, etc. Exemplary esters of methacrylic acid include methyl methacrylate, ethyl methacrylate, iso-propyl methacrylate, n-butyl methacrylate, iso-butyl methacrylate, sec-butyl methacrylate, tert-butyl methacrylate, n-hexyl methacrylate, n-octyl methacrylate, iso-octyl methacrylate, 2-ethylhexyl methacrylate, n-decyl methacrylate, etc. Preferably, the acrylate ester is butyl acrylate.

The total amount of Mannich product with phenylenediamine or derivatives thereof having at least one N—H group or phenothiazine or derivatives thereof used in the methods of the present invention as a polymerization inhibitor is that amount which is sufficient to effect inhibition of polymerization and will, of course, vary according to the particular acrylate ester and conditions under which it is used. At higher temperatures, larger amounts are generally required. Preferably, the total amount of Mannich product with phenylenediamine or derivatives thereof having at least one N—H group or phenothiazine or derivatives thereof is from about 1 ppm to about 10,000 ppm based on the weight of the acrylate ester. Most preferably, the total amount of the aforesaid compounds is from 1 ppm to about 1,000 ppm based on the weight of the acrylate ester.

The relative concentrations of Mannich product with phenylenediamine or derivatives thereof having at least one N—H group or phenothiazine or derivatives thereof are generally in the range of about 5 to about 95 weight percent Mannich product and about 95 to 5 weight percent phenylenediamine or derivatives thereof having at least one N—H group or phenothiazine or derivatives thereof based on the total combined weight of these components. It should be understood that the portion of the composition containing phenylenediamine, phenothiazine or their derivatives may be comprised either of a single compound or of combinations thereof. Preferably, the weight ratio of Mannich product to phenylenediamine or derivatives thereof having at least one N—H group or phenothiazine or derivatives thereof is about 1:3 to 3:1.

The method of the present invention can control the fouling of processing equipment, such as equipment used in the separation and purification processes of acrylate esters, which is due to or caused by the polymerization of the acrylate esters. The instant invention may be used as both a process inhibitor, which is employed during preparation and processing of the acrylate, and as a product inhibitor, which is combined with the acrylate ester in order to inhibit polymerization during storage and handling. The Mannich product with phenylenediamine or derivatives thereof having at least one N—H group or phenothiazine or derivatives thereof can be provided to the acrylate ester by any conventional method. The components can be added to the acrylate ester as a single composition containing the inhibitor compounds or the individual components can be added separately or in any other desired combination. The composition may be added as either a concentrate or as a solution using a suitable carrier solvent which is compatible with the acrylate ester.

EXAMPLES

To demonstrate the synergism which is provided by the inventive combination of compounds, the data set forth below was developed. The following examples are included as being illustrations of the invention and should not be construed as limiting the scope thereof.

The condensation reaction of a phenol, an aldehyde, and an amine is well known in the literature. Such a reaction will occur by simply heating the reaction mixture to temperatures of from 50 to 200 deg. C. and removing the water of reaction. The Mannich product used in the following examples was a commercial sample prepared by heating p-nonylphenol, ethylenediamine, and paraformaldehyde in a molar ratio of 2-1-2 in xylene until the required amount of water was removed by azeotropic distillation with the xylene. The remaining xylene was then removed and an appropriate amount of heavy aromatic naphtha added to make up a 75% active solution. This Mannich product which was used in the following examples is designated as "MP". N-Phenyl-N'-(1,4-dimethylpentyl)-p-phenylenediamine was the exemplary phenylenediamine used in the following examples and is designated as "PDP".

Evaluation of the inhibitors was carried out using butyl acrylate as a representative acrylate ester as follows: Butyl acrylate was twice distilled under vacuum, with the portion distilling at about 35–40 deg. C. being used, to remove the majority of the MEHQ inhibitor.

In a 17-mL test-tube was placed 5.0 mL of the distilled butyl acrylate and the appropriate amount of inhibitor (in a 0.02 weight/volume % solutions in xylene).

The tube was sealed with a tight fitting septum cap that was wired on. Two needles were placed in the septum and the tube purged for 50 seconds with argon. A 9-inch long, 4-mm diameter soft glass tube closed at the bottom and partly filled with mineral oil was inserted through the septum to the bottom of the test-tube. A thermocouple was then placed in the 4-mm tube and the whole set-up placed in an oil bath kept at a temperature of about 292 deg. F. The temperature of the sample was monitored on a datalogger with the time for the exothermic polymerization reaction being noted. Exotherms for samples were sharp and large, with peak temperatures being about 350 deg. F.

Generally, a set of ten samples was conducted at one time. Exotherm times varied from set to set. To relate one set to another, the ratio of the minutes-to-exotherm of each sample to that of the PDP sample (at the same ppm level in the same set) is given.

EXAMPLE 1

The principle components of the MP were evaluated in this example. EDA or a phenol (p-cresol designated as "PC") alone or in combination were ineffective as butyl acrylate inhibitors. PDP and the phenol showed the same effectiveness as the PDP alone. However, EDA and PDP showed twice the effectiveness of the PDP alone, indicating enhanced performance of the combination (Table I).

TABLE I

| Set | Compound | ppm actives | Compound | ppm actives | Minutes to Exotherm | Ratio to PDP |
|---|---|---|---|---|---|---|
| 3 | none | — | — | — | 3 | 0.1 |
|   | EDA | 2 | — | — | 4 | 0.2 |
|   | PC | 2 | — | — | 4 | 0.2 |
|   | EDA | 2 | PC | 2 | 4 | 0.2 |
|   | PDP | 2 | — | — | 24 | 1.0 |
|   | PDP | 2 | PC | 2 | 25 | 1.0 |
|   | PDP | 2 | EDA | 2 | 49 | 2.0 |
|   | PDP | 2 | EDA | 2 PC 2 | 41 | 1.7 |
| 4 | none | — | — | — | 4 | 0.1 |
|   | PDP | 3 | — | — | 74 | 1.0 |
|   | PDP | 3 | EDA | 3 | 94 | 1.3 |

EXAMPLE 2

PDP, MP, and the combination of PDP and MP were evaluated as inhibitors of butyl acrylate as described above. MP showed no effectiveness alone, whereas PDP showed good effectiveness alone. The 3:3 combination of PDP and MP showed at least triple the effectiveness of the PDP alone (Table II), an unexpected result since MP would not be expected to contribute. This result is even unexpectedly higher than the combination of PDP and EDA.

TABLE II

| Set | Compound | ppm actives | Compound | ppm actives | Minutes to Exotherm | Ratio to PDP |
|---|---|---|---|---|---|---|
| 1 | none | — | — | — | 3 | 0.1 |

TABLE II-continued

|   | Com-pound | ppm actives | Com-pound | ppm actives | Minutes to Exotherm | Ratio to PDP |
|---|---|---|---|---|---|---|
|   | MP | 3 | — | — | 5 | 0.1 |
|   | PDP | 3 | — | — | 52 | 1.0 |
|   | PDP | 3 | MP | 3 | >130 a | >2.5 |
| 6 | MP | 3 | — | — | 6 | 0.1 |
|   | PDP | 3 | — | — | 50 | 1.0 |
|   | PDP | 3 | MP | 3 | 250 | 5.0 |
| 7 | none | — | — | — | 4 | 0.2 |
|   | MP | 3 | — | — | 4 | 0.2 |
|   | MP | 3 | — | — | 5 | 0.3 |
|   | MP | 3 b | — | — | 5 | 0.3 |
|   | PDP | 3 | — | — | 17 | 1.0 |
|   | PDP | 3 | MP | 3 | 123 | 7.2 |
|   | PDP | 3 | MP | 3 b | 85 | 5.0 | a. The reaction was not monitored for longer than 130 minutes and the exotherm occurred after 130 minutes.
b. An error was made in the preparation of the solution and the stated ppm level is believed to be correct.

EXAMPLE 3

Several different ratios of PDP to MP were evaluated in this example. At all of the different ratios, the combinations of PDP and MP were at least twice as effective as the PDP alone (Table III). The optimum ratio of PDP:MP appears to be at about 1:1.

TABLE III

| Set | Com-pound | ppm actives | Com-pound | ppm actives | Minutes to Exotherm | Ratio to PDP |
|---|---|---|---|---|---|---|
| 2 | none | — | — | — | 5 | 0.2 |
|   | MP | 2 | — | — | 5 | 0.2 |
|   | PDP | 2 | — | — | 21 | 1.0 |
|   | PDP | 2 | MP | 2 | 91 | 4.3 |
|   | PDP | 2 | MP | 6 | 84 | 4.0 |
|   | MP | 6 | — | — | 7 | 0.1 |
|   | PDP | 6 | — | — | 62 | 1.0 |
|   | PDP | 6 | MP | 2 | 233 | 3.7 |
|   | PDP | 6 | MP | 6 | 565 | 9.0 |
| 8 | none | — | — | — | 3 | 0.3 |
|   | PDP | 3 | — | — | 10 | 1.0 |
|   | PDP | 3 | MP | 1 | 32 | 3.2 |
|   | PDP | 3 | MP | 2 | 56 | 5.6 |
|   | PDP | 3 | MP | 3 | 66 | 6.6 |
|   | PDP | 3 | MP | 4 | 72 | 7.2 |
|   | PDP | 3 | MP | 5 | 70 | 7.0 |
|   | PDP | 3 | MP | 6 | 67 | 6.7 |
| 4 | none | — | — | — | 4 | 0.1 |
|   | PDP | 3 | — | — | 74 | 1.0 |
|   | PDP | 3 | MP | 2 a | 143 | 1.9 |
| 5 | none | — | — | — | 4 | 0.1 |
|   | PDP | 3 | — | — | 59 | 1.0 |
|   | PDP | 3 | MP | 2 a | 100 | 1.7 |
| 6 | none | — | — | — | 5 | 0.2 |
|   | MP | 2 a | — | — | 5 | 0.2 |
|   | PDP | 3 | — | — | 33 | 1.0 |
|   | PDP | 3 | MP | 2 a | 100 | 3.0 |

From the above two examples, it can be seen that the MP enhances the effectiveness of the PDP while the MP does not have any effectiveness alone. These data are summarized in Table IV.

TABLE IV

| Ratio of PDP-MP | Average Ratio of Exotherms Combination: PDP |
|---|---|
| 3-1 | 3.5:1 |
| 3-2 | 3.1:1 |
| 3-3 | 6.1:1 |
| 3-4 | 7.2:1 |
| 3-5 | 7.0:1 |
| 3-6 | 6.7:1 |
| 3-9 | 4.0:1 |

EXAMPLE 4

These three tests were conducted in the presence of air in the test-tube. The data show that even in the presence of oxygen the PDP-MP combination is about twice as effective as PDP alone (Table V).

TABLE V

| Set | Com-pound | ppm actives | Com-pound | ppm actives | Minutes to Exotherm | Ratio to PDP |
|---|---|---|---|---|---|---|
| 5 | none | — | — | — | 3 air | 0.2 |
|   | PDP | 3 | — | — | 20 air | 1.0 |
|   | PDP | 3 | MP | 2 a | 38 air | 1.8 |

An error was made in the preparation of the solution and the stated ppm level is believed to be correct.

EXAMPLE 5

Phenothiazine (PTZ) was effective alone, but efficacy was enhanced at least three-fold by the addition of MP to the PTZ (Table VI). The combination of PTZ and PDP were additive, but addition of MP to a combination of these materials showed a twenty-fold enhancement of efficacy.

TABLE VI

| Set | Com-pound | ppm actives | Com-pound | ppm actives | Minutes to Exotherm | Ratio to PDP |
|---|---|---|---|---|---|---|
| 6 | none | — | — | — | 5 | 0.2 |
|   | PTZ | 3 | — | — | 37 | 1.1 |
|   | MP | 2 a | — | — | 5 | 0.2 |
|   | PDP | 3 | — | — | 33 | 1.0 |
|   | PTZ | 3 | MP | 2 a | 97 | 3.0 |
| 7 | none | — | — | — | 4 | 0.2 |
|   | PDP | 3 | — | — | 17 | 1.0 |
|   | PTZ | 3 | — | — | 31 | 1.8 |
|   | PTZ | 3 | PDP | 3 | 43 | 2.5 |
| 8 | none | — | — | — | 3 | 0.3 |
|   | PTZ | 3 | — | — | 12 | 1.2 |
|   | PDP | 3 | — | — | 10 | 1.0 |
|   | PTZ | 3 | PDP | 3 MP 3 | 200 | 20.0 |

An error was made in the preparation of the solution and the stated ppm level is believed to be correct.

EXAMPLE 6

Acrylate esters are produced by reacting a certain acid with an alcohol. The final product will contain some amount of unreacted acid which is substantially removed upon purification. However, depending upon the degree of purification, a small amount of acid may remain with the acrylate ester end product. The following table represents the results of testing conducted to determine the efficacy of the instant invention as a polymerization inhibitor where various concentrations of acids are present in the acrylate ester.

TABLE VII

| Percent Acrylic Acid (Balance is butyl acrylate) | Com-pound | ppm | Com-pound | ppm | Minutes to Exotherm |
|---|---|---|---|---|---|
| 20 | None | 0 | — | — | 9 |
| 20 | MP | 20 | — | — | 13 |
| 20 | PDP | 20 | — | — | 10 |
| 20 | PDP | 20 | MP | 20 | 18 |
| 10 | None | 0 | — | — | 11 |
| 10 | MP | 20 | — | — | 8 |
| 10 | PDP | 20 | — | — | 17 |
| 10 | PDP | 20 | MP | 20 | 45 |
| 5 | None | 0 | — | — | 9 |
| 5 | MP | 20 | — | — | 7 |
| 5 | PDP | 20 | — | — | 37 |
| 5 | PDP | 20 | MP | 20 | 127 |
| 2 | None | 0 | — | — | 7 |

TABLE VII-continued

| Percent Acrylic Acid (Balance is butyl acrylate) | Compound | ppm | Compound | ppm | Minutes to Exotherm |
|---|---|---|---|---|---|
| 2 | MP | 20 | — | — | 6 |
| 2 | PDP | 20 | — | — | 74 |
| 2 | PDP | 20 | MP | 20 | 220 |
| 0 | None | 0 | — | — | 5, 5 |
| 0 | MP | 20 | — | — | 6, 7 |
| 0 | PDP | 20 | — | — | 972, 1162 |
| 0 | PDP | 20 | MP | 20 | 972(a), 1222 |

(a) The exotherm was not recorded on the datalogger. However, the visual viscosity of the sample was much less than the PDP sample with exotherm of 972, which result indicates that the exotherm was 972.

While this invention has been described with respect to particular embodiments thereof, it is apparent that numerous other forms and modifications will be obvious to those skilled in the art. The appended claims generally should be construed to cover all such obvious forms and modifications which are within the true spirit and scope of the present invention.

What is claimed is:

1. A method for inhibiting acrylate monomer polymerization during processing at elevated temperatures comprising adding to said acrylate monomer a polymerization inhibitor in an effective amount for the purpose of:
   (a) A Mannich product prepared from a substituted phenol having the formula

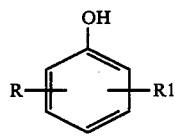

wherein R and $R_1$ are the same or different and are independently selected from the group consisting of hydrogen, hydroxy, alkyl, aryl, alkaryl, aralkyl and alkoxy groups of from 1 to about 20 carbon atoms and both R and $R_1$ cannot be hydrogen, an aldehyde having the formula

wherein R2 is selected from the group consisting of hydrogen or alkyl groups having from 1 to about 6 carbon atoms, and
ethylenediamine, wherein the molar ratio of substituted phenol:ethylenediamine:aldehyde is in the range of 0.5–5:1:0.5–5 and
   (b) a phenylenediamine or derivative thereof having the formula

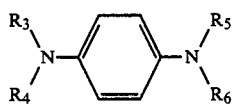

wherein $R_3$, $R_4$, $R_5$ and $R_6$ are the same or different and are hydrogen, alkyl, aryl, alkaryl or aralkyl groups with the proviso that at least one of $R_3$, $R_4$, $R_5$ or $R_6$ is hydrogen, and/or phenothiazine or derivatives thereof having the formula

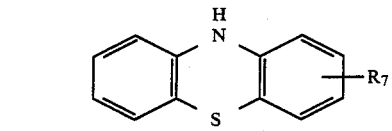

wherein $R_7$ is hydrogen or alkyl, wherein the weight ratio of said Mannich product to said phenylenediamine or derivative thereof or said phenothiazine or derivative thereof is from about 1:19 to about 19:1.

2. A method according to claim 1 wherein said substituted phenol is p-nonylphenol.

3. A method according to claim 1 wherein said aldehyde is paraformaldehyde.

4. A method according to claim 1 wherein said acrylate monomer is selected from the group consisting of n-alkyl, secondary and branched chain alkyl esters of acrylic acid and methacrylic acid.

5. A method according to claim 1 wherein said acrylate monomer is n-butyl acrylate.

6. A method according to claim 1 wherein one of said phenylenediamine derivatives is N-phenyl-N'-(1,4-dimethylpentyl)-p-phenylenediamine.

7. A method according to claim 1 wherein the total concentration of said polymerization inhibitor is 1 to 10,000 parts per million based on the weight of said acrylate monomer.

8. A method according to claim 1 wherein the total concentration of said polymerization inhibitor is 1 to 1,000 parts per million based on the weight of said acrylate monomer.

9. A method according to claim 1 wherein the weight ratio of said Mannich product to said phenylenediamine or derivatives thereof or phenothiazine or derivatives thereof is from about 1:3 to about 3:1.

10. A method according to claim 1 wherein said polymerization inhibitor is added as a concentrate to said acrylate monomer.

11. A method according to claim 1 wherein said polymerization inhibitor in solution is added to said acrylate monomer.

12. A method according to claim 11 wherein said solution comprises a solvent which is compatible with said acrylate monomer.

13. A method for inhibiting acrylate monomer polymerization during storage and handling after processing comprising adding to said acrylate monomer a polymerization inhibitor in an effective amount for the purpose of:
   (a) a Mannich product prepared form a substituted phenol having the formula

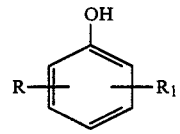

wherein R and $R_1$ are the same or different and are independently selected from the group consisting of hydrogen, hydroxy, alkyl, aryl, alkaryl, aralkyl and alkoxy groups of from 1 to about 20 carbon atoms and both R and $R_1$ cannot be hydrogen, an aldehyde having the formula

wherein $R_2$ is selected from the group consisting of hydrogen or alkyl groups having from 1 to about 6 carbon atoms, and ethylenediamine, wherein the molar ratio of substituted phenol:ethylenediamine:aldehyde is in the range of 0.5–5:1:0.5–5 and (b) a phenylenediamine or derivatives thereof having the formula

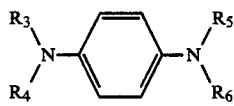

wherein $R_3$, $R_4$, $R_5$ and $R_6$ are the same or different and are hydrogen, alkyl, aryl, alkaryl or aralkyl groups with the proviso that at least one of $R_3$, $R_4$, $R_5$ or $R_6$ is hydrogen, and/or phenothiazine or derivatives thereof having the formula

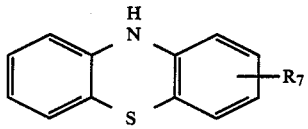

wherein $R_7$ is hydrogen or alkyl wherein the weight ratio of said Mannich product to said phenylenediamine or derivative thereof or said phenothiazine or derivative thereof is from about 1:19 to about 19:1.

14. A method according to claim 13 wherein said substituted phenol is p-nonylphenol.

15. A method according to claim 13 wherein said aldehyde is paraformaldehyde.

16. A method according to claim 13 wherein said acrylate monomer is selected from the group consisting of n-alkyl, secondary and branched chain alkyl esters of acrylic acid and methacrylic acid.

17. A method according to claim 13 wherein said acrylate monomer is n-butyl acrylate.

18. A method according to claim 13 wherein one of said phenylenediamine derivatives is N-phenyl-N'-(1,4-dimethylpentyl)-p-phenylenediamine.

19. A method according to claim 13 wherein the total concentration of said polymerization inhibitor is from about 1 to about 10,000 parts per million based on the weight of said acrylate monomer.

20. A method according to claim 13 wherein the total concentration of said polymerization inhibitor is from about 1 to about 1,000 parts per million based on the weight of said acrylate monomer.

21. A method according to claim 13 wherein the weight ratio of said Mannich product to said phenylenediamine or derivatives thereof or said phenothiazine or derivatives thereof is from about 1:3 to about 3:1.

22. A method according to claim 13 wherein said polymerization inhibitor is added as a concentrate to said acrylate monomer.

23. A method according to claim 13 wherein said polymerization inhibitor in solution is added to said acrylate monomer.

24. A method according to claim 23 wherein said solution comprises a solvent which is compatible with said acrylate monomer.

25. A composition for inhibiting the polymerization of acrylate monomers comprising (a) a Mannich product prepared from a substituted phenol having the formula

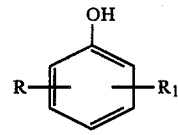

wherein R and $R_1$ are the same or different and are independently selected from the group consisting of hydrogen, hydroxy, alkyl, aryl, alkaryl, aralkyl and alkoxy groups of from 1 to about 20 carbon atoms and both R and $R_1$ cannot be hydrogen, an aldehyde having the formula

wherein $R_2$ is selected from the group consisting of hydrogen or alkyl groups having from 1 to about 6 carbon atoms, and ethylenediamine wherein the molar ration of substituted phenol:ethylenediamine:aldehyde is in the range of 0.5–5:1:0.5–5 and (b) a phenylenediamine or derivative thereof having the formula

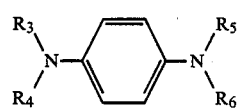

wherein $R_3$, $R_4$, $R_5$ and $R_6$ are the same or different and are hydrogen, alkyl, aryl, alkaryl or aralkyl groups with the proviso that at least one of $R_3$, $R_4$, $R_5$ or $R_6$ is hydrogen, and/or phenothiazine or derivatives thereof having the formula

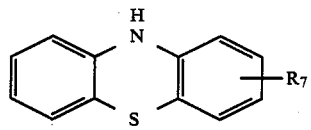

wherein $R_7$ is hydrogen or alkyl, wherein the weight ratio of said Mannich product to said phenylenediamine or derivative thereof or said phenothiazine or derivative thereof is from about 1:19 to about 19:1.

26. A composition according to claim 25 wherein said substituted phenol is p-nonylphenol.

27. A composition according to claim 25 wherein said aldehyde is paraformaldehyde.

28. A composition according to claim 25 wherein said phenylenediamine derivative is N-phenyl-N'-(1,4 dimethylpentyl)-p-phenylenediamine.

29. A composition according to claim 25 wherein the weight ratio of said Mannich product to said phenylenediamine or derivative thereof or said phenothiazine or derivative thereof is from about 1:3 to about 3:1.

30. A method for inhibiting acrylonitrile polymerization during processing at elevated temperatures comprising adding to said acrylonitrile a polymerization inhibitor in an effective amount for the purpose of:

(a) A Mannich product prepared from a substituted phenol having the formula

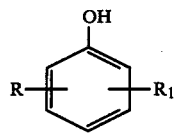

wherein R and R₁ are the same or different and are independently selected from the group consisting of hydrogen, hydroxy, alkyl, aryl, alkaryl, aralkyl or alkoxy groups of from 1 to about 20 carbon atoms and both R and R, cannot be hydrogen.

an aldehyde having the formula

wherein R2 is selected from hydrogen or alkyl groups having from 1 to about 6 carbon atoms, and ethylenediamine wherein the molar ratio of substituted phenol:ethylenediamine:aldehyde is in the range of 0.5–5:1:0.5–5, and (b) a phenylenediamine or derivatives thereof having the formula

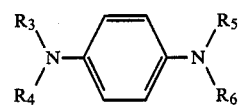

wherein R3, R4, R5, R6 are the same or different and are hydrogen, alkyl, aryl, alkaryl or aralkyl groups with the proviso that at least one of R3, R4, R5 or R6 is hydrogen, and/or phenothiazine or derivatives thereof having the formula

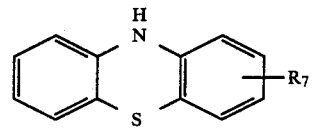

wherein R₇ is hydrogen or alkyl wherein the weight ratio of said Mannich product to said phenylenediamine or derivative thereof or said phenothiazine or derivative thereof is from about 1:19 to about 19:1.

31. A method according to claim 30 wherein said substituted phenol is p-nonylphenol.

32. A method according to claim 30 wherein said aldehyde is paraformaldeyhyde

33. A method according to claim 30 wherein one of said phenylenediamine derivatives is N-phenyl-N'-(1,4 dimethylpentyl)-p-phenylenediamine.

34. A method according to claim 30 wherein the total concentration of said polymerization inhibitor is from about 1 to about 1,000 parts per million based on the weight of said acrylonitrile.

35. A method according to claim 30 wherein the total concentration of said polymerization inhibitor is from about 1 to about 1,000 parts per million based on the weight of said acrylonitrile.

36. A method according to claim 30 wherein the weight ratio of said Mannich product to said phenylenediamine or derivatives thereof or said phenothiazine or derivatives thereof is from about 1:3 to about 3:1.

* * * * *